United States Patent [19]
O'Neill et al.

[11] Patent Number: 5,403,281
[45] Date of Patent: Apr. 4, 1995

[54] INLINE HEAT EXCHANGER AND CARDIOPLEGIA SYSTEM

[75] Inventors: William G. O'Neill; Timothy P. Walker, both of Ann Arbor, Mich.

[73] Assignee: Minnesota Mining and Manufacturing Company, St. Paul, Minn.

[21] Appl. No.: 951,725

[22] Filed: Sep. 25, 1992

[51] Int. Cl.$^6$ .......................... A61F 7/12; F28D 7/12
[52] U.S. Cl. ................................. 604/113; 607/106; 165/156
[58] Field of Search .............. 604/113, 114; 165/154–156, 158; 128/399, 400; 607/96, 104–106

[56] References Cited

U.S. PATENT DOCUMENTS

| | | | |
|---|---|---|---|
| 2,434,519 | 1/1948 | Raskin | 257/262 |
| 3,289,756 | 12/1966 | Jaeger | 165/158 |
| 3,374,066 | 3/1968 | Farrant | 23/258.5 |
| 3,374,832 | 3/1968 | Tucker | 165/158 |
| 3,551,641 | 12/1970 | Truhan | 604/113 X |
| 3,612,059 | 10/1971 | Ersek | 128/399 |
| 4,177,816 | 12/1979 | Torgeson | 128/400 |
| 4,183,213 | 1/1980 | Rao | 60/517 |
| 4,705,505 | 11/1987 | Fried | 604/80 |
| 4,759,749 | 7/1988 | Verkaart | 604/113 |
| 4,846,177 | 7/1989 | Leonard | 128/400 |
| 4,878,537 | 11/1989 | Verkaart | 165/156 |
| 4,927,412 | 5/1990 | Menasche | 604/96 |

OTHER PUBLICATIONS

Incropera and DeWitt, "Introduction to Heat Transfer" (John Wiley and Sons, 1985), pp. 467, 468.
Brochure entitled "Plain and Simple" From 3M Health Care (Form No. 78-8067-3788-4), 1991.
Brochure entitled "Sarns Conducer heat exchanger—Technical Compedium"; Aug. 1, 1991, 3M Health Care (Form No. 78-8067-3506-0).
Brochure entitled "Integrating the essentials . . . " 3M Health Care; (Form No. 78-8067-4263-7) 1991.
Incorpera and DeWitt; "Introduction to Heat Transfer"; at pp. 461 and 602 (John Wiley and Sons, 1990).

*Primary Examiner*—John D. Yasko
*Assistant Examiner*—Adam J. Cermak
*Attorney, Agent, or Firm*—Gary L. Griswold; Walter N. Kirn; Stephen W. Bauer

[57] ABSTRACT

A flexible-resilient heat exchanger that is designed to be disposed inline of a cardioplegia tubing set for heating or cooling blood and/or cardioplegia solution. The heat exchanger comprises a flexible-resilient inner tube defining an inner flow path for blood and/or cardioplegia solution, for example, and a flexible-resilient outer tube surrounding the inner tube. The outer tube has fluid inlet and outlet ports so as to define an outer flow path between the inner and outer tubes for heat exchanging fluid, for example. The outer tube is sealingly connected to the inner tube adjacent opposite ends of the outer flow path, and the inner tube defining a barrier between the first and second fluids while permitting heat transfer between the first and second fluids.

34 Claims, 4 Drawing Sheets

INLINE HEAT EXCHANGER AND CARDIOPLEGIA SYSTEM

This invention relates to cardioplegia administration systems used during heart surgery, and more particularly to a heat exchanger for use in such systems.

BACKGROUND OF THE INVENTION

Typically, a circulatory support and cardioplegia administration system includes (among other things) a venous catheter for draining blood from the patient's venous system, a venous line for transferring blood drained with the venous catheter to a venous reservoir, a heat exchanger and an oxygenator connected via a transfer line to the outlet of the venous reservoir, and an arterial line connected to the outlet of the oxygenator to supply the oxygenated blood to a cannula, which returns the blood to the patient's heart. Such systems have included other components or subsystems as well. One such subsystem relates to blood recovery from the surgical site (e.g., the pericardial sack), and that system would include a number of blood suction devices (intracardiac suckers) that supply blood to a cardiotomy reservoir that collects, defoams and filters the recovered blood before supplying it to the venous reservoir of the main system.

Another subsystem is the cardioplegia administration system. Cardioplegia is a commonly used technique for protecting the heart during heart surgery. Typically, cooled cardioplegia solution (e.g., a potassium solution, cooled blood or a blood/potassium solution) is administered to the patient's heart in either the antegrade or retrograde direction through either the patient's aorta or coronary sinus, respectively. "Antegrade" refers to the direction of normal blood flow, and "retrograde" refers to the direction opposite of normal blood flow.

The cardioplegia solution stops the heart and reduces its temperature to minimize damage to the heart during surgery. Such cardioplegia solutions are typically introduced into the heart in an intermittent fashion. For example, a bolus of cooled cardioplegia solution may be delivered to the heart to initially arrest the heart, and then the subsequent doses of the cardioplegia may be administered approximately every 15-20 minutes.

Cardioplegia subsystems have included a heat exchanger connected to a source of cardioplegia solution and/or blood, a bubble trap to collect air emboli to prevent supplying such emboli to the patient, a temperature monitor for measuring and displaying the temperature of the cardioplegia solution downstream of the heat exchanger, a cardioplegia supply line connected to the outlet of the bubble trap/temperature monitor, and a catheter connected to the downstream end of the cardioplegia supply line for supplying the cardioplegia solution to the heart. Suitable catheters for retrograde administration of cardioplegia are disclosed in U.S. Pat. No. 4,927,412 (Menasche), and U.S. patent application Ser. No. 07/874,589, filed Apr. 27, 1992, on "Retrograde Coronary Sinus Catheter", by William G. O'Neill, Nelson L. Huldin, Sheila J. Hanson and John A. Covert, both of which are hereby incorporated by reference.

Heretofore, the cardioplegia heat exchanger has been separated from the patient by the substantial length (e.g., 8 feet (2.4 m)) of the cardioplegia supply line (plus the bubble trap/temperature monitor). A substantial volume of cardioplegia solution is held in the cardioplegia supply line, and this solution is being warmed by heat transfer through the cardioplegia supply line while it remains in that line. The result is that the initial cardioplegia solution being administered to the patient may be warmer than desired so that more cardioplegia solution must be administered to keep the temperature of the heart down. In addition to the delay in cooling the heart, the additional cardioplegia solution required due to this warming results in administering additional quantities of a drug (potassium solution) to the patient than would otherwise be required.

One approach to this problem has been to recirculate the cardioplegia solution in the cardioplegia delivery line back to the heat exchanger to re-cool it. That approach involves opening a clamp on a recirculation line when the delivery line is closed adjacent the catheter.

SUMMARY OF THE INVENTION

This invention provides a novel heat exchanger that is disposed inline of the cardioplegia supply line or arterial line to cool the blood and/or cardioplegia solution immediately before it is returned or administered to the patient. The heat exchanger is adapted to be manipulated (e.g., flexed) to bring the downstream end of the heat exchanger close to the surgical site to reduce the volume of cardioplegia solution in the tubing set downstream of the heat exchanger. The prime required for the heat exchanger is substantially reduced in comparison to conventional heat exchangers.

Generally, the heat exchanger comprises a flexible-resilient inner tube defining an inner flow path for a first fluid comprising one of (a) blood and/or cardioplegia solution, and (b) heat exchanging fluid, and a flexible-resilient outer tube surrounding the inner tube. The outer tube has fluid inlet and outlet ports so as to define an outer flow path between the inner and outer tubes for a second fluid comprising the other of (a) blood and/or cardioplegia solution, and (b) heat exchanging fluid. The outer tube is sealingly connected to the inner tube adjacent opposite ends of the outer flow path. The inner tube defines a barrier between the first and second fluids while permitting heat transfer between the first and second fluids.

In one aspect of the invention, the inner tube has a generally cruciform cross section defining the inner flow path as having a generally cruciform cross section, and an outer surface defining a plurality of channels through which the second fluid is allowed to flow.

In another aspect of the invention, the inner tube has an outer surface with a plurality of grooves spirally formed therein through which the second fluid is allowed to flow. The outer surface of the inner tube is provided with a plurality of raised ribs separating the spiral grooves, with the raised ribs of the inner tube engaging the inner surface of the outer tube to contain the outer flow path through the spiral grooves. The outer tube has a generally round cross section co-axial with the inner tube. The plurality of spiral grooves preferably comprises two to four spiral grooves, with each spiral groove having a generally rectangular cross section defined by its longer sides extending generally in the radial direction.

In yet another aspect of the invention, the inner tube comprises two inner tubes, each having a generally flattened, oval or rectangular cross section.

Preferably, the inner and outer tubes are formed of polymeric material that allows the entire heat exchanger to be flexed, and the opposite ends of the outer flow path are separated longitudinally along the heat exchanger by at least 1.8 meters (6 feet).

The inline heat exchanger of the invention preferably constitutes a part of a cardioplegia administration set for administering cardioplegia to a patient's heart during cardiopulmonary surgery. The set comprises a flexible-resilient fluid supply tube having a lumen for supplying cardioplegia and/or blood to a patient's heart, and a catheter connected to the downstream end of the fluid supply tube and having a lumen in fluid communication with the lumen of the fluid supply tube. The catheter is adapted to be inserted into the patient to supply cardioplegia to the patient's heart. The inline heat exchanger forms a portion of the fluid supply tube. Preferably, the inline heat exchanger forms a substantial portion of the fluid supply tube generally adjacent the downstream end of the fluid supply tube, with one of the inner and outer fluid paths of the inline heat exchanger constituting a portion of the lumen of the fluid supply tube.

These and other features will be pointed out hereinafter.

BRIEF DESCRIPTION OF THE DRAWING

The invention will be further described with reference to the drawing wherein corresponding reference characters indicate corresponding parts throughout the several views of the drawing, and wherein.

DETAILED DESCRIPTION OF PREFERRED EMBODIMENTS

Figure 1:
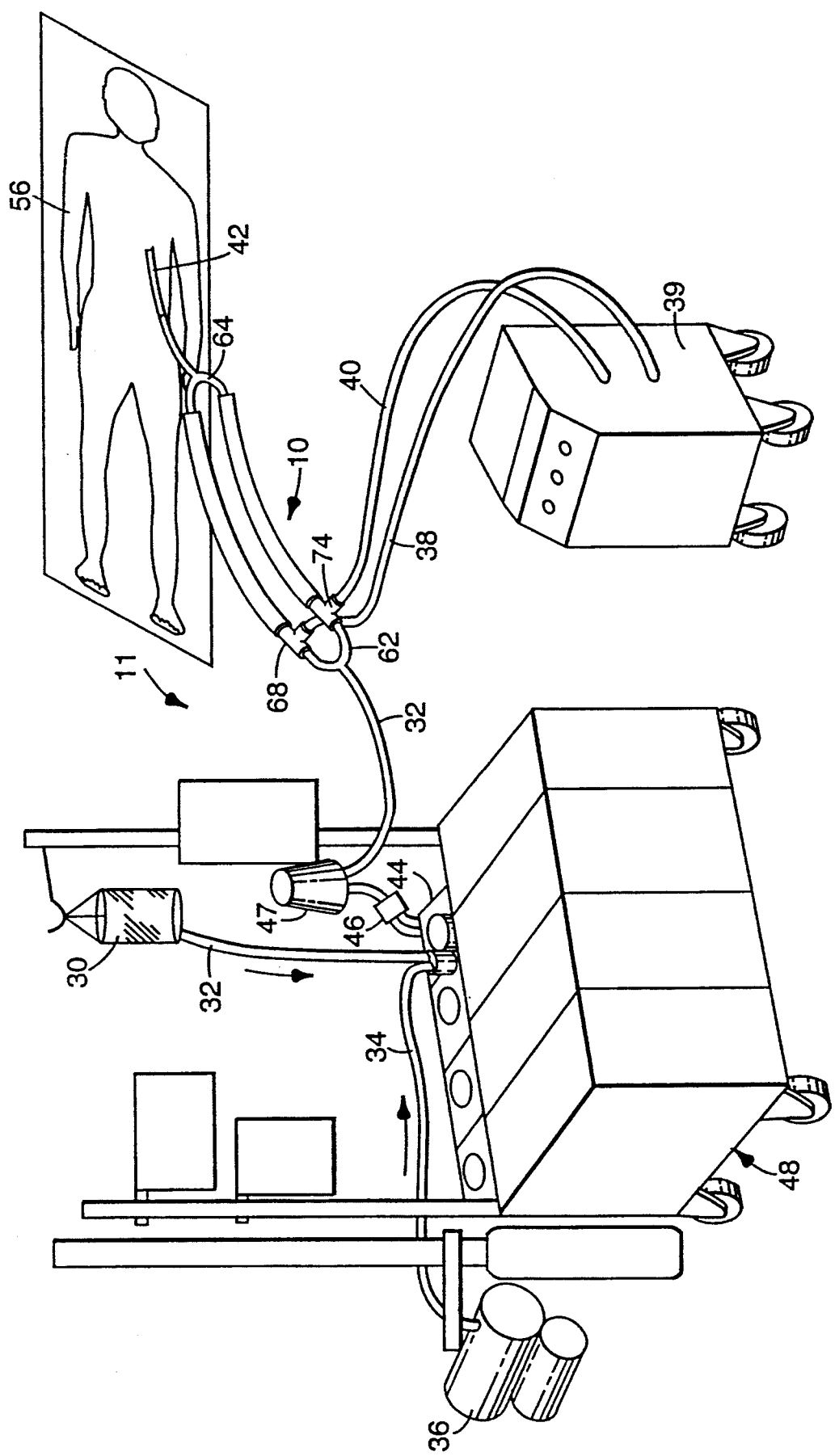
FIG. 1 is a diagrammatic view of a circulatory support and cardioplegia administration system including a novel inline heat exchanger of the invention.

Now referring to the drawing, a heat exchanger of the invention is designated in its entirety by the reference numeral 10, 110 or 210, depending upon whether it is the embodiment shown in FIGS. 1-4, 5-7 or 8, respectively. The heat exchanger 10, 110 or 210 is adapted for heating or cooling blood and/or cardioplegia solution for use during heart surgery.

The heat exchanger 10, 110 or 210 generally comprises a flexible-resilient inner tube 12A–D, 112 or 212, and a flexible-resilient outer tube 14A–B, 114 or 214 surrounding the inner tube 12A–D, 112 or 212. The inner tube 12A–D, 112 or 212 defines an inner flow path 16, 116 or 216 for a first fluid comprising one of (a) blood and/or cardioplegia solution, and (b) heat exchanging fluid. The outer tube 14A–B, 114 or 214 has fluid inlet and outlet ports 18 or 118 and 20 or 120 so as to define an outer flow path 22, 122 or 222 between the inner and outer tubes 12A–D, 112,212 and 14A–B, 114 or 214 for a second fluid comprising the other of (a) blood and/or cardioplegia solution, and (b) heat exchanging fluid. The outer tube 14A–B, 114 or 214 is sealingly connected to the inner tube 12A–D, 112 or 212 adjacent opposite ends 24 or 124 and 26 or 126 of the outer flow path 22, 122 or 222. The inner tube 12A–D, 112 or 212 defines a barrier (also 12A–D, 112 or 212) between the first and second fluids while permitting heat transfer between the first and second fluids.

FIG. 1 illustrates the basic layout of the cardioplegia administration system generally designated 11. That system includes a drug bag 30 for supplying conventional cardioplegia solution via cardioplegia supply line 32 to the heat exchanger 10, blood supply line 34 for supplying blood from the circulatory support circuit (the heat exchanger/blood oxygenator of which are indicated at 36) to cardioplegia supply tubing 32, and water supply lines 38 and 40 for supplying water from the water source 39 to the outer flow path 22 of the heat exchanger 10 and draining water from outer flow path 22 of the heat exchanger 10. It will be understood that water or sterile saline solution constitutes the preferred heat exchanging fluid for use in the heat exchanger 10.

A cardioplegia catheter indicated generally at 42 supplies blood and/or cardioplegia solution to the patient's heart from the downstream end 64 of the heat exchanger 10. The cardioplegia catheter 42 may be of the antegrade or retrograde type. Suitable catheters for retrograde administration of cardioplegia are disclosed in U.S. Pat. No. 4,927,412, and U.S. patent application Ser. No. 07/874,589, filed Apr. 27, 1992, on "Retrograde Coronary Sinus Catheter", by William G. O'Neill, Nelson L. Huldin, Sheila J. Hansen and John A. Covert, both of which are hereby incorporated by reference.

The blood supply line 34 and cardioplegia supply line 32 conventionally run through a blood pump 44, such as a positive displacement roller pump (also 44), to pump the blood and/or cardioplegia solution at a specified rate. A mixing valve indicated at 46 is provided for mixing the blood and/or cardioplegia solution. A conventional bubble trap 47 is normally provided in the cardioplegia supply line 32 to collect air bubbles.

The perfusion system indicated generally at 48 may be of the type sold under the trade designation "SARNS 9000" Perfusion System by Minnesota Mining and Manufacturing Company, St. Paul, Minn. The perfusion system 48 is used to pump fluids, monitor various measurements, and control both the circulatory support system and the cardioplegia administration system 11.

The circulatory support system comprises a venous line (not shown) for draining blood from the patient's venous system and providing that blood to a venous reservoir (not shown). Blood is then pumped from the venous reservoir via one of the pump modules in the perfusion system 48 to the heat exchanger/blood oxygenator 36. Oxygenated blood from the outlet of the heat exchanger/blood oxygenator 36 is then returned to the patient's arterial system via an arterial line (not shown) and arterial cannula (not shown). Oxygenated blood from the heat exchanger/blood oxygenator 36 is also supplied to the cardioplegia administration system 11 via the blood supply line 34.

A blood scavenging subsystem (not shown) is also provided to recover blood from the surgical field for reuse. The blood scavenging system includes one or more intracardiac suckers for draining blood from the pericardial sack, and a cardiotomy reservoir to collect, defoam and filter the scavenged blood. The outlet of the cardiotomy reservoir is connected to an inlet for the venous reservoir to supply the scavenged blood to the venous reservoir for re-use.

Figure 2:
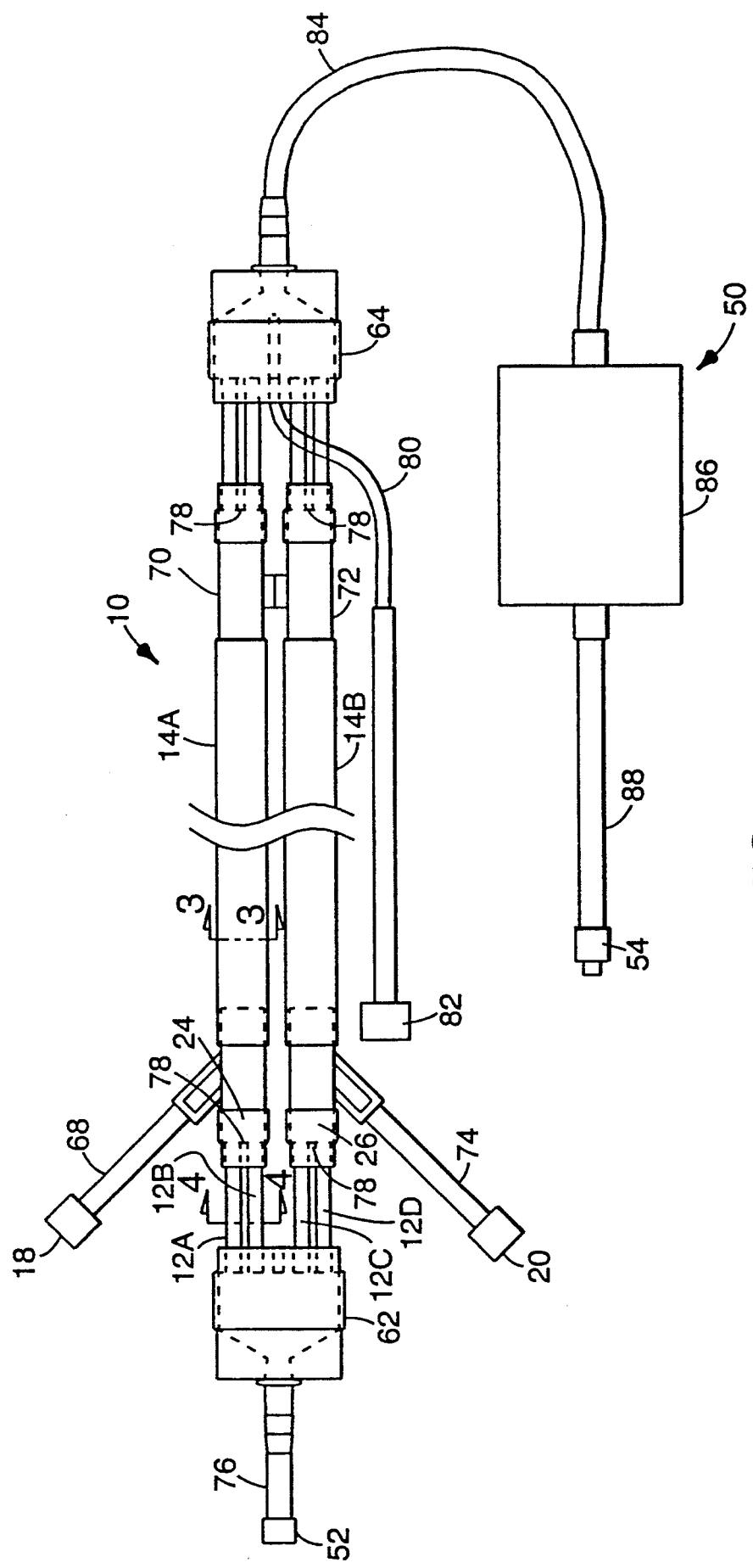
FIG. 2 is a side view of the inline heat exchanger of FIG. 1.

FIG. 2 shows a cardioplegia administration tubing set 50 comprising at its upstream end 52 a female luer (also 52), which is connected to tubing leading to a blood pump, such as the positive displacement roller pump 44 shown in FIG. 1, to supply blood and/or cardioplegia solution to the tubing set 50. At its downstream end 54, the cardioplegia administration tubing set 50 comprises a male luer (also 54) which is connected to a cardioplegia catheter (indicated at 42 in FIG. 1) for administering blood and/or cardioplegia solution to the heart of the patient 56. The direction of blood and/or cardioplegia solution flow in FIG. 2 is from the female luer 52 through the heat exchanger 10 to the male luer 54.

Figure 3:
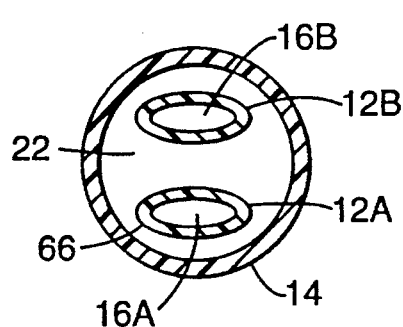
FIG. 3 is a cross-sectional view substantially along line 3—3 of FIG. 2.
Figure 4:
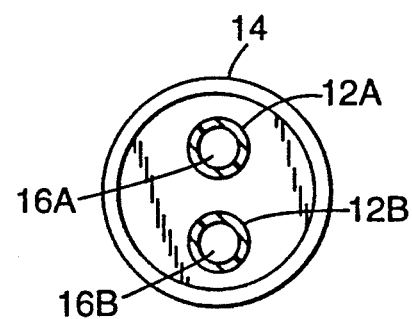
FIG. 4 is a cross-sectional view substantially along line 4—4 of FIG. 2.

The heat exchanger 10 includes two outer, elongate tubes 14A and 14B (which are sometimes collectively referred to by the reference numeral 14) extending substantially between two manifolds 62 and 64, constituting the upstream and downstream manifolds relative to the inner flow path 16. Four inner tubes, e.g., 12A, 12B, 12C and 12D, are provided, with two inner tubes passing through each of the outer tubes 14A and 14B. The inner tubes 12A-D are sometimes collectively referred to by the reference numeral 12. The portion 66 of the inner tubes 12A-D contained within the outer tubes 14A and 14B have a generally flattened, oval or rectangular cross section as illustrated in FIG. 3.

The lumens (also 16) of the inner tubes 12A-D define the inner flow path 16, and the passageway (at 22) defined between the outer surface of the inner tubes 12A-D and the inner surface of the outer tubes 14A and 14B defines the outer flow path 22.

The water path 22 through the heat exchanger 10 begins at inlet Y-connector 68 mounted at the upstream end of outer tube 14A, with water passing through the outer tube 14A in the downstream direction to a double T-fitting 70 and 72 mounted on the downstream end of the outer tube 14A. The double T-fitting 70, 72 bridges between the two outer tubes 14A and 14B so that water passes through the double T-fitting 70, 72 into the second outer tube 14B. Water exits the second outer tube 14B through an outlet Y-connector 74.

The inlet Y-connector 68 is connected to the water supply line 38, and the outlet Y-connector 74 is connected to the water supply line 40 to circulate water from the water source 39. Water source 39 includes conventional heating and/or refrigerating means (not shown) to control the temperature of the water being used as a heat exchanging fluid.

The blood and/or cardioplegia path 16 through the cardioplegia tubing set 50 begins at the female luer 52 which is mounted on a short section of tubing 76. The downstream end of the short section of tubing 76 is mounted on the upstream fitting of the upstream manifold 62. The upstream manifold 62 preferably has four outlets mounted on the upstream ends of the four inner tubes 12A-D. Blood passes through the four inner tubes 12A-D to their downstream ends which are mounted in the downstream manifold 64.

The arrangement is such that the blood and/or cardioplegia path 16 is split at the upstream manifold 62 into four paths, e.g., 16A and 16B in FIG. 3, through the inner tubes 12A-D, and the four paths are rejoined at the downstream manifold 64. Four fittings 78 are provided for sealing the ends of the outer tubes 14A and 14B around the inner tubes 12A-D.

The length of the heat exchanger 10 between the upstream and downstream manifolds 62 and 64 is most preferably approximately 1.83 meters (72 inches), with the outer tubes 14A and 14B taking up most of this length. The inner tubes 12A-D each have a length of approximately 1.83 meters, and the unflattened portion (FIG. 4) of the inner tubes 12A-D have an internal diameter of approximately 4.6 mm (0.18 inches) and a wall thickness of approximately 0.38 mm (0.015 inches). The wall thickness of the inner tubes 12A-D may be approximately 0.51 mm (0.02 inches), although heat transfer through PVC inner tubes 12A-D is more efficient with the thinner wall thickness (e.g., 0.38 mm (0.015 inches).

The flattened portion 66 of each inner tube 12A-D may be flattened so that the internal cross section (FIG. 3) of each inner tube 12A-D has a longer dimension of approximately 8.9 mm (0.35 inch) and a shorter dimension of approximately 1.27 mm (0.05 inch). The inner tubes 12A-D may be extruded round, and flattened by a heat forming process. The outer tubes 14A and 14B may have an inside diameter of approximately 9.5 mm (⅜ inch) and a wall thickness of approximately 1.6 mm (1/16 inch).

An electronic thermistor indicated at 80 is provided in the downstream manifold 64 to monitor the temperature of the blood and/or cardioplegia solution, and a conventional connector 82 is provided for electrical connection of the thermistor 80 to a monitor in the perfusion system 48. A suitable electronic thermistor 80 is available under Part No. 4491 from Yellow Springs Instruments, Inc., Yellow Springs, Ohio.

The downstream end of the downstream manifold 64 is connected to tubing 84 leading to a conventional PTFE membrane air removal filter 86. Another section of tubing 88 is connected to the downstream end of the air removal filter 86 and the male luer 54. The cardioplegia catheter 42 is connected to the male luer connector 54. Tubing 84 may be PVC tubing having a 4.8 mm (3/16 inch) inside diameter, a 1.27 mm (1/16 inch) wall thickness, and a 80 mm (3 inch) length; and tubing 88 may be PVC tubing having a 4.8 mm (3/16 inch) inside diameter, 1.27 mm (1/16 inch) wall thickness, and a 300 mm (12 inch) length.

The various parts of the heat exchanger 10 may be formed of any suitable medical grade polymeric materials, including polyvinyl chloride (PVC), polyurethane, and PTFE for tubing, manifolds, fittings and connectors and polycarbonate or acrylic for luer fittings, so long as the heat exchanger 10 is resiliently-flexible in use. The manifold, tubing, fittings and connectors of the heat exchanger 10 and cardioplegia tubing set 50 are conveniently solvent bonded together to form one integral unit.

Preferably, the inline heat exchanger 10 comprises an integral part of the fluid supply tube set 50. As used herein, "integral part" means forming a one piece molding or construction that is not designed to be mechanically assembled by the hospital staff. For example, the inline heat exchanger 10 can be solvent bonded to adjacent tube sections to form an integral part of the fluid supply tube set 50.

A heat exchanger, similar to heat exchanger 10, can alternately be formed with a single outer tube containing two inner tubes.

Figure 5:
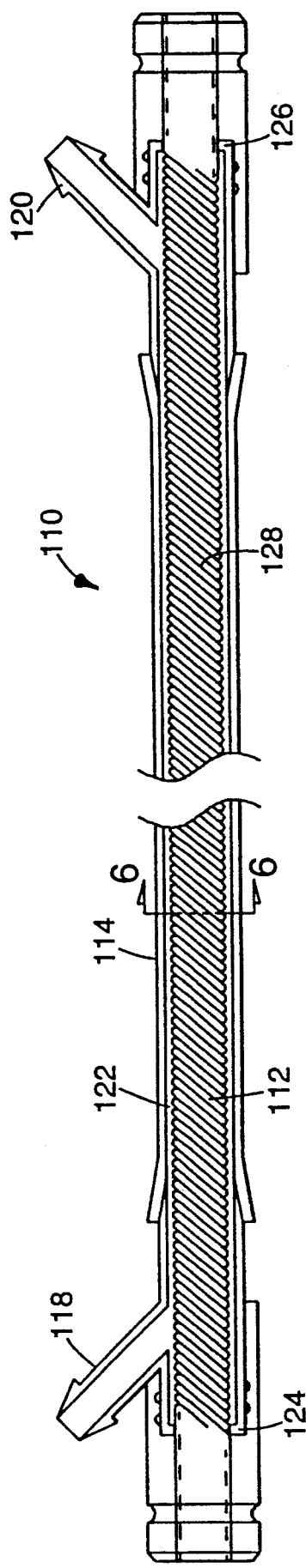
FIG. 5 is a side view of an alternative embodiment of the inline heat exchanger.
Figure 7:
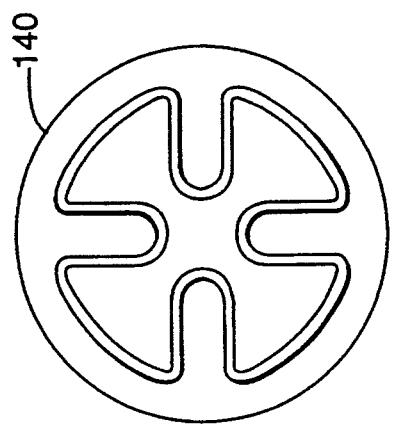
FIG. 7 is an end view of an extrusion die that may be used to extrude an inner tube for the heat exchanger of FIGS. 5 and 6.
Figure 6:
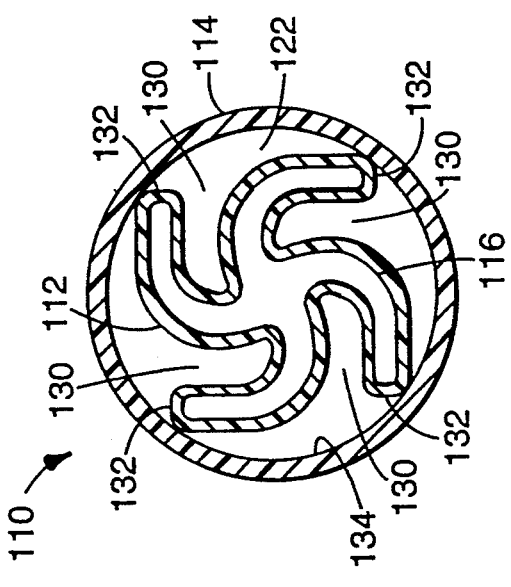
FIG. 6 is a cross-sectional view substantially along line 6—6 of FIG. 5.

In heat exchanger 110 illustrated in FIGS. 5–7, the inner tube 112 has an outer surface 128 with a plurality of spiral grooves 130 formed therein through which the second fluid is allowed to flow, and a plurality of raised ribs 132 separating the spiral grooves 130. The raised ribs 132 of the inner tube 112 engage the inner surface 134 of the outer tube 114 to contain the outer flow path 122 through the spiral grooves 130. The outer tube 114 has generally round cross section generally co-axial with the inner tube 112.

Most preferably, the plurality of spiral grooves 130 comprises two-to-four spiral grooves 130, with each spiral groove 130 having a generally rectangular cross section defined by its longer sides extending generally in the radial direction, as illustrated in FIG. 6.

For example, four spiral grooves 130 may be provided as illustrated in FIG. 6, each having an elongate cross section having an area of approximately 5 mm$^2$ so that the outer flow path 122 has a total cross sectional area of approximately 20 mm$^2$. This compares to the internal cross sectional area of approximately 18 mm$^2$ for the cardioplegia supply line (similar to cardioplegia supply line 32) supplying fluid to the outer flow path 122 (which is the same as the internal cross sectional area of the tubing draining the outer flow path 122). It will be observed that the velocity of fluid through the outer flow path 122 is reduced as the overall cross sectional area of the outer flow path 122 is increased.

The spiral grooves 130 preferably spiral around the inner tube 112 at a helix angle of approximately 30-60 degrees. For example, the helix angle may be approximately 45 degrees and the length of the heat exchanger 110 between the ends 124 and 126 of the outer flow path 122 may be approximately 1.83 meters (72 inches), so that the length of each groove 130 is approximately 2.59 meters (102 inches). It will be observed that the effective length of the outer flow path 122 is reduced as the helix angle of the spiral grooves 130 is increased, assuming that the length of the outer tubing 114 remains the same.

Preferably, the inner and outer tubes 112 and 114 are formed of generally transparent polymeric material, such as polyvinyl chloride (PVC). For example, the inner and outer tubes 112 and 114 may be extruded of PVC material, assembled together and solvent bonded adjacent the ends 124 and 126 of the outer tube 114. FIG. 7 illustrates the configuration of an extrusion die 140 that may be used to extrude the inner tube 112. The extrusion die 140 may be rotated relative to the extruded portion of the inner tube to provide the appropriate helix angle as discussed above.

As an alternative embodiment based on the heat exchanger 110 illustrated in FIGS. 5-6, the inner tube 112 may be generally opaque and the outer tube 114 may be generally transparent. In this alternative, the inner flow path 114 is adapted for heat exchanging fluid and the outer flow path 122 is adapted for blood and/or cardioplegia solution. The arrangement is such as to facilitate visualization of the blood and/or cardioplegia flow through the outer flow path 122 without distraction by the flow of heat exchanging fluid through the inner flow path 114.

Figure 8:
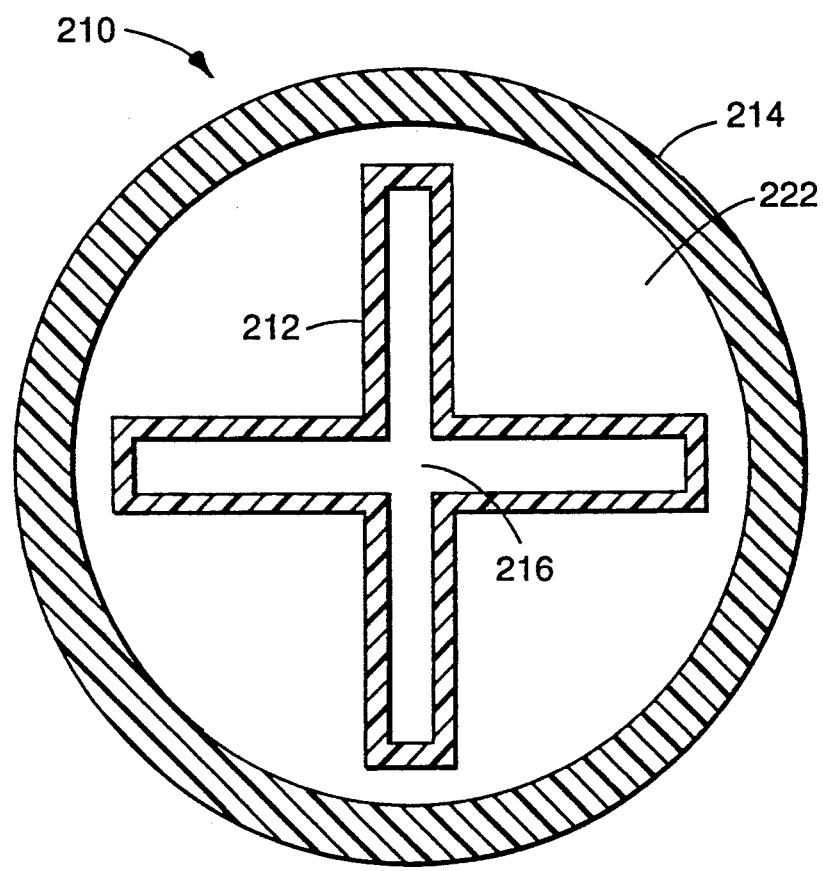
FIG. 8 is a cross-sectional view similar to FIGS. 3 and 6, illustrating details of yet another embodiment of the inline heat exchanger.

As illustrated in FIG. 8, the inner tube 212 of the heat exchanger 210 has a generally cruciform cross section defining the inner flow path 216 as having a generally cruciform cross section, and an outer surface defining a plurality of channels through which the second fluid is allowed to flow. An outer flow path 222 is defined between the outer surface of the inner tube 212 and the inner surface of the outer tube 214.

In heat exchanger 210, it is contemplated that the inner flow path 216 would be the blood and/or cardioplegia solution flow path, and the outer flow path 222 would be the water flow path. The inner and outer tubes 212 and 214 are preferably extruded of suitable medical grade polymeric material (e.g., polyvinyl chloride (PVC)) to allow the heat exchanger to be flexed, and the parts of the heat exchanger 210 are preferably solvent bonded inline of the cardioplegia administration tubing set to form one integral unit.

The flattened cross sectional configuration of the outer and/or inner flow paths illustrated in FIGS. 3, 6 and 8 is believed to improve heat transfer efficiency of the heat exchanger 10, 110 and 210 relative to designs not having such flattened or finger-like cross sectional portions, while reducing the amount of blood or cardioplegia solution required to prime the heat exchanger 10, 110 or 210.

The blood and/or cardioplegia solution path should be designed to provide laminar flow at the desired flow rates (e.g., 100-400 ml/minute) of the blood and/or cardioplegia solution to reduce hemolysis, and the water path is preferably designed to provide turbulent flow at the desired water flow rates (e.g., 5-20 liters/minute) to increase heat transfer. By providing narrow flattened or finger-like cross sectional portions (e.g., the flattened portions 66 of the inner tubes 12A-D) for the blood and/or cardioplegia solution path, the solution is kept close to the fluid barrier (e.g., 12A-D) throughout its cross section to facilitate heat transfer across the fluid barrier (e.g., 12A-D). Such close proximity to the fluid barrier (e.g., 12A-D) is less important in the case of the water path due to the turbulent flow of water through that path.

The heat exchangers 10, 110 and 210 are separated at most from the patient 56 by a short distance. For example, the downstream end 64 of the heat exchanger 10 is only approximately 46 centimeters (18 inches) in comparison to the length of the heat exchanger 10 itself, which is about 1.8 meters (72 inches). As a result, the volume of blood and/or cardioplegia solution downstream of the heat exchanger 10 is very small so that the volume of warmed cardioplegia solution is initially administered to the patient's heart is kept very small as well.

The prime required for the heat exchangers 10, 110, and 210 is also small in comparison to most conventional cardioplegia heat exchangers. This is because the heat exchanger forms an integral part of the cardioplegia supply line.

As various changes could be made in the above constructions without departing from the scope of the invention, it is intended that all matter contained in the description above or shown in the accompanying drawing shall be interpreted as illustrative and not in a limiting sense.

We claim:

1. A heat exchanger for heating or cooling blood and/or cardioplegia solution, the heat exchanger comprising
    a flexible-resilient inner tube defining an inner flow path for a first fluid comprising one of (a) blood and/or cardioplegia solution, and (b) heat exchanging fluid; and
    a flexible-resilient outer tube surrounding the inner tube and having fluid inlet and outlet ports so as to define an outer flow path between the inner and outer tubes for a second fluid comprising the other of (a) blood and/or cardioplegia solution, and (b) heat exchanging fluid, the outer tube being sealingly connected to the inner tube adjacent opposite ends of the outer flow path;

the inner tube defining a barrier between the first and second fluids while permitting heat transfer between the first and second fluids; and the inner and outer tubes each being formed of resiliently-flexible material that allows the entire heat exchanger to be flexed.

2. A heat exchanger according to claim 1 further comprising means for mounting a cardioplegia catheter in fluid communication with one of the first and second flow paths to administer blood and/or cardioplegia to the heart.

3. A heat exchanger according to claim 1 wherein the inner tube has a generally cruciform cross section defining the inner flow path as having a generally cruciform cross section, and an outer surface defining a plurality of channels through which the second fluid is allowed to flow.

4. A heat exchanger according to claim 1 wherein the inner tube has an outer surface with a plurality of grooves spirally formed therein through which the second fluid is allowed to flow.

5. A heat exchanger according to claim 4 wherein the outer tube has an inner surface, and the outer surface of the inner tube is provided with a plurality of raised ribs separating the spiral grooves, the raised ribs of the inner tube engaging the inner surface of the outer tube to contain the outer flow path through the spiral grooves.

6. A heat exchanger according to claim 5 wherein the outer tube has a generally round cross section co-axial with the inner tube.

7. A heat exchanger according to claim 6 wherein the plurality of spiral grooves comprises two to four spiral grooves, each spiral groove having a generally rectangular cross section defined by its longer sides extending generally in the radial direction.

8. A heat exchanger according to claim 6 wherein the inner flow path is adapted for heat exchanging fluid and the outer flow path is adapted for blood and/or cardioplegia solution, the inner tube being generally opaque and the outer tube being generally transparent.

9. A heat exchanger according to claim 1 wherein the inner tube has a cross-sectional configuration selected from a group consisting of generally flattened, oval and rectangular cross sections.

10. A heat exchanger according to claim 9 wherein the inner tube comprises a first inner tube and the inner flow path comprises a first inner flow path, the heat exchanger further comprising a second inner tube enclosed by the outer tube, the second inner tube defining a second inner flow path for the first fluid, the outer tube being sealing connected to both the first and second inner tubes to define the outer flow path as being outside the inner tubes but inside the outer tube.

11. A heat exchanger according to claim 14 wherein the inner tube has a cross-sectional configuration selected from a group consisting of generally flattened, oval and rectangular cross sections.

12. A heat exchanger according to claim 11 wherein the inner tube comprises a first inner tube and the inner flow path comprises a first inner flow path, the heat exchanger further comprising a second inner tube enclosed by the outer tube, the second inner tube defining a second inner flow path for the first fluid, the outer tube being sealing connected to both the first and second inner tubes to define the outer flow path as being outside the inner tubes but inside the outer tube.

13. A heat exchanger according to claim 14 wherein the polymeric material is selected from a group consisting of polyvinyl chloride, polyurethane and polytetrafluoroethylene.

14. A heat exchanger for heating or cooling blood and/or cardioplegia solution, the heat exchanger comprising a flexible-resilient inner tube defining an inner flow path for a first fluid comprising one of (a) blood and/or cardioplegia solution, and (b) heat exchanging fluid; and a flexible-resilient outer tube surrounding the inner tube and having fluid inlet and outlet ports so as to define an outer flow path between the inner and outer tubes for a second fluid comprising the other of (a) blood and/or cardioplegia solution, and (b) heat exchanging fluid, the outer tube being sealingly connected to the inner tube adjacent opposite ends of the outer flow path;

the inner tube defining a barrier between the first and second fluids while permitting heat transfer between the first and second fluids; and the inner and outer tubes each being formed of polymeric material that allows the entire heat exchanger to be flexed.

15. A heat exchanger according to claim 11 wherein the opposite ends of the outer flow path are separated longitudinally along the heat exchanger by at least 1.8 meters.

16. A heat exchanger according to claim 14 further comprising means for mounting a cardioplegia catheter in fluid communication with one of the first and second flow paths to administer blood and/or cardioplegia to the heart.

17. A heat exchanger according to claim 14 wherein the inner tube has a generally cruciform cross section defining the inner flow path as having a generally cruciform cross section, and an outer surface defining a plurality of channels through which the second fluid is allowed to flow.

18. A heat exchanger according to claim 14 wherein the inner tube has an outer surface with a plurality of grooves spirally formed therein through which the second fluid is allowed to flow.

19. A heat exchanger according to claim 18 wherein the outer tube has an inner surface, and the outer surface of the inner tube is provided with a plurality of raised ribs separating the spiral grooves, the raised ribs of the inner tube engaging the inner surface of the outer tube to contain the outer flow path through the spiral grooves.

20. A heat exchanger according to claim 19 wherein the outer tube has a generally round cross section co-axial with the inner tube.

21. A heat exchanger according to claim 20 wherein the plurality of spiral grooves comprises two to four spiral grooves, each spiral groove having a generally rectangular cross section defined by its longer sides extending generally in the radial direction.

22. A heat exchanger according to claim 20 wherein the inner flow path is adapted for heat exchanging fluid and the outer flow path is adapted for blood and/or cardioplegia solution, the inner tube being generally opaque and the outer tube being generally transparent.

23. A cardioplegia administration set for administering cardioplegia to a patient's heart during cardiopulmonary surgery, the set comprising:
- a flexible-resilient fluid supply tube having a lumen and upstream and downstream ends for supplying cardioplegia and/or blood to a patient's heart; and
- a catheter connected to the downstream end of the fluid supply tube and having a lumen in fluid communication with the lumen of the fluid supply tube, the catheter being adapted to be inserted into the patient to supply cardioplegia to the patient's heart;
- the fluid supply tube including an inline heat exchanger for heating or cooling blood and/or cardioplegia solution passing through the fluid supply tube, the heat exchanger comprising a flexible-resilient inner tube defining an inner flow path for a first fluid comprising one of (a) the blood and/or cardioplegia solution, and (b) heat exchanging fluid; and a flexible-resilient outer tube surrounding the inner tube and having fluid inlet and outlet ports so as to define an outer flow path between the inner and outer tubes for a second fluid comprising the other of (a) the blood and/or cardioplegia solution, and (b) the heat exchanging fluid, the outer tube being sealingly connected to the inner tube adjacent opposite ends of the outer flow path, the inner tube defining a barrier between the first and second fluids while permitting heat transfer between the first and second fluids, one of the inner and outer fluid flow paths constituting a portion of the lumen of the fluid supply tube, the inner and outer tubes each being formed of polymeric material that allows the entire heat exchanger to be flexed.

24. A cardioplegia administration set according to claim 23 wherein the inner tube has a generally cruciform cross section defining the inner flow path as having a generally cruciform cross section, and an outer surface defining a plurality of channels through which the second fluid is allowed to flow.

25. A cardioplegia administration set according to claim 23 wherein the outer tube has an inner surface, the inner tube having an outer surface with a plurality of grooves spirally formed therein through which the second fluid is allowed to flow, and a plurality of raised ribs separating the spiral grooves, the raised ribs of the inner tube engaging the inner surface of the outer tube to contain the outer flow path through the spiral grooves, the outer tube having generally a round cross section co-axial with the inner tube.

26. A cardioplegia administration set according to claim 25 wherein the plurality of spiral grooves comprises two to four spiral grooves, each spiral groove having a generally rectangular cross section defined by its longer sides extending generally in the radial direction.

27. A cardioplegia administration set according to claim 25 wherein the inner flow path is adapted for heat exchanging fluid and the outer flow path is adapted for blood and/or cardioplegia solution, the inner tube being generally opaque and the outer tube being generally transparent.

28. A cardioplegia administration set according to claim 23 wherein the inner tube has a cross-sectional configuration selected from a group consisting of generally flattened, oval and rectangular cross sections.

29. A cardioplegia administration set according to claim 28 wherein the inner tube comprises a first inner tube and the inner flow path comprises a first inner flow path, the heat exchanger further comprising a second inner tube enclosed by the outer tube, the second inner tube defining a second inner flow path for the first fluid, the outer tube being sealing connected to both the first and second inner tubes to define the outer flow path as being outside the inner tubes but inside the outer tube.

30. A cardioplegia administration set according to claim 23 wherein the polymeric material is selected from a group consisting of polyvinyl chloride, polyurethane and polytetrafluoroethylene.

31. A cardioplegia administration set for administering cardioplegia to a patient's heart during cardiopulmonary surgery, the set comprising:
- a flexible-resilient fluid supply tube having a lumen and upstream and downstream ends for supplying cardioplegia and/or blood to a patient's heart; and
- a catheter connected to the downstream end of the fluid supply tube and having a lumen in fluid communication with the lumen of the fluid supply tube, the catheter being adapted to be inserted into the patient to supply cardioplegia to the patient's heart;
- the fluid supply tube including an inline heat exchanger for heating or cooling blood and/or cardioplegia solution passing through the fluid supply tube, the heat exchanger comprising a flexible-resilient inner tube defining an inner flow path for a first fluid comprising one of (a) the blood and/or cardioplegia solution, and (b) heat exchanging fluid; and a flexible-resilient outer tube surrounding the inner tube and having fluid inlet and outlet ports so as to define an outer flow path between the inner and outer tubes for a second fluid comprising the other of (a) the blood and/or cardioplegia solution, and (b) the heat exchanging fluid, the outer tube being sealingly connected to the inner tube adjacent opposite ends of the outer flow path, the inner tube defining a barrier between the first and second fluids while permitting heat transfer between the first and second fluids, one of the inner and outer fluid flow paths constituting a portion of the lumen of the fluid supply tube;
- the inner and outer tubes each being formed of polymeric material that allows the entire heat exchanger to be flexed, the opposite ends of the outer flow path being separated longitudinally along the heat exchanger by at least 1.8 meters.

32. A heat exchanger for heating or cooling medical fluid for administration to a patient, the heat exchanger comprising
- a flexible-resilient inner tube defining an inner flow path for a first fluid comprising one of (a) the medical solution, and (b) heat exchanging fluid, the inner tube having a cross-sectional configuration selected from a group consisting of generally flattened, oval and rectangular cross sections; and
- a flexible-resilient outer tube surrounding the inner tube and having fluid inlet and outlet ports so as to define an outer flow path between the inner and outer tubes for a second fluid comprising the other of (a) the medical solution, and (b) heat exchanging fluid, the outer tube being sealingly connected to the inner tube adjacent opposite ends of the outer flow path;
- the inner tube defining a barrier between the first and second fluids while permitting heat transfer between the first and second fluids;

the inner and outer tubes each being formed of polymeric material that allows the entire heat exchanger to be flexed.

33. A heat exchanger according to claim 32 wherein the inner tube comprises a first inner tube and the inner flow path comprises a first inner flow path, the heat exchanger further comprising a second inner tube enclosed by the outer tube, the second inner tube defining a second inner flow path for the first fluid, the outer tube being sealing connected to both the first and second inner tubes to define the outer flow path as being outside the inner tubes but inside the outer tube.

34. A heat exchanger according to claim 32 wherein the polymeric material is selected from a group consisting of polyvinyl chloride, polyurethane and polytetrafluoroethylene.

* * * * *

UNITED STATES PATENT AND TRADEMARK OFFICE
CERTIFICATE OF CORRECTION

PATENT NO. : 5,403,281

DATED : April 4, 1995

INVENTOR(S) : William G. O'Neill and Timothy P. Walker

It is certified that error appears in the above-indentified patent and that said Letters Patent is hereby corrected as shown below:

Col. 10, line 29, "11" should read --14--.

Signed and Sealed this

Second Day of April, 1996

Attest:

BRUCE LEHMAN

Attesting Officer

Commissioner of Patents and Trademarks